United States Patent
Singer et al.

(10) Patent No.: US 10,478,455 B2
(45) Date of Patent: Nov. 19, 2019

(54) THERAPEUTIC USE OF TETRATHIOMOLYBDATE

(71) Applicant: UCL BUSINESS LTD, London (GB)

(72) Inventors: Mervyn Singer, Greater London (GB); John Francis Martin, Greater London (GB); Alex Peter Dyson, Greater London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 13/630,180

(22) Filed: Sep. 28, 2012

(65) Prior Publication Data

US 2013/0177659 A1    Jul. 11, 2013

Related U.S. Application Data

(63) Continuation-in-part of application No. PCT/GB2011/050653, filed on Mar. 30, 2011.

(30) Foreign Application Priority Data

Mar. 30, 2010 (GB) .................................. 1005394.0
Oct. 4, 2011 (EP) ..................................... 11183830

(51) Int. Cl.
*A61K 33/24* (2019.01)

(52) U.S. Cl.
CPC ..................... *A61K 33/24* (2013.01)

(58) Field of Classification Search
CPC ................. A61K 33/00; A61K 33/24
See application file for complete search history.

(56) References Cited

U.S. PATENT DOCUMENTS

| | | | |
|---|---|---|---|
| 6,703,050 B1 | 3/2004 | Brewer et al. | |
| 2004/0009237 A1 | 1/2004 | Brewer | |
| 2006/0039995 A1 | 2/2006 | Frey, II et al. | |
| 2007/0207191 A1* | 9/2007 | Kanzer | A61K 9/14 424/449 |
| 2008/0031817 A1* | 2/2008 | Mazar | C12Q 1/26 424/9.2 |
| 2008/0213396 A1 | 9/2008 | Brewer | |

FOREIGN PATENT DOCUMENTS

| | | |
|---|---|---|
| JP | 2002524426 A | 8/2002 |
| WO | 0013712 A2 | 3/2000 |
| WO | 03075910 A1 | 9/2003 |
| WO | WO 03/099223 A2 | 12/2003 |
| WO | WO 2004/017957 A1 | 3/2004 |
| WO | WO 2006/020727 A2 | 2/2006 |

(Continued)

OTHER PUBLICATIONS

Coucouvanis et al., reactivity and kinetic studies of (NH4)2(MoS4) in acidic aqueous solution possible relevance to the angiostatic of the MoS42-ligand, J. Inorg. Biochem., 2009, vol. 103, pp. 143-155.*

(Continued)

*Primary Examiner* — Lakshmi S Channavajjala
(74) *Attorney, Agent, or Firm* — Saliwanchik, Lloyd & Eisenschenk

(57) ABSTRACT

Tetrathiomolybdate is for use in therapy of a condition requiring reduced metabolism of an organ or whole body, e.g. myocardial infection, stroke or ischaemia-reperfusion injury.

13 Claims, 4 Drawing Sheets

(56) References Cited

FOREIGN PATENT DOCUMENTS

| WO | WO 2007/084818 A2 | 7/2007 | |
|---|---|---|---|
| WO | WO2008070741 | * 6/2008 | ............ A61K 31/54 |
| WO | WO 2008/100653 A2 | 8/2008 | |
| WO | WO 2011/121354 A1 | 10/2011 | |

OTHER PUBLICATIONS

Nicholson, hydrogen sulfide and ischemia-reperfusion injury, Pharmacol. Res. 2010, vol. 62, pp. 289-297.*

Dorweiler et al. (Ischemia Reperfusion injury, Pathophysiology and clinical implications, Eur. J. Trauma and Emerg. Surg., 2007, vol. 6, p. 600-612) (Year: 2007).*

Thurman (Triggers of inflammation after renal ischemia/prefusion, Clinical Immunology, 2007, vol. 123, p. 7-13) (Year: 2007).*

Kleinig et al. (Suppression of inflammation in ischemic and hemorrhagic stroke: therapeutic options, Current Opinion in Neurology, 2009, vol. 22, pp. 294-231) (Year: 2009).*

Hassouneh, B. et al. "Tetrathiomolybdate promotes tumor necrosis and prevents distant metastases by suppressing angiogenesis in head and neck cancer", *Molecular Cancer Therapeutics*, Mar. 2007, vol. 6, No. 3, pp. 1039-1045.

Hou. G. et al. "Tetrathiomolybdate protects against cardiac damage by doxorubicin in mice", *Journal of Laboratory and Clinical Medicine*, Nov. 1, 2005, vol. 146, No. 5, pp. 299-303.

Mandinov, L. et al. "Inhibition of in-stent restenosis by oral copper chelation in porcine coronary arteries", *American Journal of Physiology—Heart and Circulatory Physiology*, Dec. 2006, vol. 291, No. 6, pp. H2692-H2697.

Wei, H. et al. "Copper chelation by tetrathiomolybdate inhibits lipopolysaccharide-induced inflammatory responses in vivo" *American Journal of Physiology—Heart and Circulatory Physiology*, Sep. 1, 2011, vol. 301, No. 3, pp. H712-H720.

Lukaski, Henry C. et al. "Body temperature and thyroid hormone metabolism of copper-deficient rats," *Journal of Nutritional Biochemistry*, 1995, vol. 6, p. 445-451.

Umezu, Gokichi et al. "Topics on Major Trace Metal Elements and Their Prescription 8," *The Journal of Practical Pharmacy*, 1996, vol. 47, No. 2, p. 81-84.

Haouzi, Philippe et al., "$H_2S$ induced hypometabolism in mice is missing in sedated sheep," *Respiratory Physiology & Neurobiology*, 2008, 160:109-115.

Simon, Florian et al., "Hemodynamic and Metabolic Effects of Hydrogen Sulfide During Porcine Ischemia/Reperfusion Injury," *Shock*, 2008, 30(4):359-364.

Whiteman, Philip K. et al., *Chemistry, Biochemistry and Pharmacology of Hydrogen Sulfide*, Springer, 2015, pp. 339, 340, 341, and 356.

Jingyu, Zhou, "Influence of Moderate Copper Deficiency Induced by Tetrathiomolybdate on the Response to the Artery Balloon Injury of Rats." Chinese selected Doctoral dissertations, MAster's theses full-text Darabase (CDMD) (Doctor), technology of medicine and hygiene, Dec. 15, 2006, 12th issue, E062-30.

Brewer, G.J., et al., "Treatment of Wilson Disease With Ammonium Tetrathiomolybdate: III. Initial Therapy in a Total of 55 Neurologically Affected Patients and Follow-up With Zinc Therapy." Arch Neurol., 2003, 60: 379-385.

Brewer, G.J., et al., "Treatment of Wilson Disease With Ammonium Tetrathiomolybdate: IV. Comparison of Tetrathiomolybdate and Trientine in a Double-blind Study of Treatment of the Neurologic Presentation of Wilson Disease." Arch Neurol., 2006, 63: 521-527.

Brewer, G.J., et al., "Treatment of Wilson's disease with tetrathiomolybdate: V. control of free copper by tetrethiomolybdate and a comparison with trientine." Translational Research, 2009, 154(2): 70-77.

Chan, C.M., et al., "Pharmacologic evaluation of ammonium tetrathiomolybdate after intravenous and oral administration to healthy dogs." Am. J. Vet. Res., May 2015, 76(5): 445-453.

Dyson, A., et al., "Ammonium tetrathiomolybdate following ischemia/reperfusion injury: Chemistry, pharmacology, and impact of a new class of sulfide donor in preclinical injury models." PLOS Medicine, 2017, 14(7): e1002310.

Erlinge, D., et al., "Rapid Endovascular Catheter Core Cooling Combined With Cold Saline as an Adjunct to Percutaneous Coronary Intervention for the Treatment of Acute Myocardial Infarction." Journal of the American College of Cardiology, 2014, 63(18): 1857-1865.

Gooneratne, S.R., et al., "An investigation of the effects of intravenous administration of thiomolybdate on copper metabolism in chronic Cu-poisoned sheep." Br. J. Nutr., 1981, 46: 469-480.

Gooneratne, S.R., et al., "Intravenous administration of thromolybdate for the prevention and treatment of chronic copper poisoning in sheep." Br. J. Nutr., 1981, 46: 457-467.

Goetberg, M., et al., "A Pilot Study of Rapid Cooling by Cold Saline and Endovascular Cooling Before Reperfusion in Patients With ST-Elevation Myocardial Infarction." Cric Cardiovasc Interv., 2010, 3: 400-407.

Howell, J.M., et al., "Effect of Intravenously Administered Tetrathiomolybdate on Plasma Copper Concentrations of Copper-loaded Sheep." J. Comp. Path., 1990, 103: 321-334.

Lee, H.-L., et al , "Biphasic modulation of the mitochondrial electron transport chain in myocardial ischemia and reperfusion." Am J Physiol Heart Circ Physiol, 2012, 302: H1410-H1422.

Okada, M. et al., "Decoppering effect of Tetrathiomolybdate (TTM) in the patients with Wilson disease." Biomed Res Trace Elements, 1998, 9(3): 155-156.

Shiming, Y., "Practical Elements Medicine," p. 221.

Zhao, X., et al., "Endothelium-Derived Nitric Oxide Regulates Postichemic Myocardial Oxygenation and Oxygen Consumption by Modulation of Mitochondrial Electron Transport." Circulation, 2005, 111: 2966-2972.

Bose, A.K., et al., "Glucagon-like Peptide 1 Can Directly Protect the Heart Against Ischemia/Reperfusion Injury." Diabetes, Jan. 2005, 54: 146-151.

Brewer, G.J., et al., "Treatment of Metastatic Cancer with Tetrathiomolybdate, an Anticopper, Antiangiogenic Agent: Phase I Study." Clinical Cancer Research, Jan. 2000, 6: 1-10.

Childs, E.W., et al., "Hypothermia Reduces Microvascular Permeability and Reactive Oxygen Species Expression after Hemorrhagic Shock." J Trauma, 2005, 58: 271-277.

Eltzschig, H.K., et al., "Vascular ischaemia and reperfusion injury." British Medical Bulletin, 2004, 70: 71-86.

Frank, A., et al., "Myocardial ischemia reperfusion injury—from basic science to clinical bedside." Semin Cardiothorac Vasc Anesth, Sep. 2012, 16(3): 123-132.

Hausenloy, D.J., et al., "Myocardial ischemia-reperfusion injury: a neglected therapeutic target" The Journal of Clinical Investigation, Jan. 2013, 123(1): 92-100.

Haverich, A., et al., "Organ protection during hypothermic circulatory arrest" The Journal of Thoracic and Cardiovascular Surgery, Mar. 2003, 125: 460-462.

Henderson, A.H., "Disease of the Heart." Second Edition, W.B. Saunders Company Limited, 1996, pp. 57-60 and 62.63.

L'Her, E., et al., "Effects of mild induced hypothermia during experimental sepsis." Cult Care Med, 2006, 34(10): 2621-2623.

Muizelaar, J.P., "Cerebral Ischemia-Reperfusion Injury After Severe Head Injury and Its Possible Treatment With Polyethyleneglycol-Superoxide Dismutase." Annals of Emergency Medicine, Jun. 1992, 22(6): 1014-1021.

Ning, X.H., et al., "Hypothermia preserves myocardial function and mitochondrial protein gene expression during hypoxia." Am J Physiol Heart Circ Physiol, 2003, 285: H212-H219.

Redman, B.G., et al., "Phase II Trial of Tetrathiomolybdate in Patients with Advanced Kidney Cancer." Clinical Cancer Research, May 2003, 9(5): 1666-1672.

Riksen, N.P., et al., "The Effect of EPLerenone on Ischemia Reperfusion Injury in Human mroCARDium (EPLICARD)." ClinicalTrials.gov, Apr. 2014, Radboud University Medical Centre, Nijmegen, Gelderland, Netherlands, 6500HB, <https://clinicaltrials.gov/ct2/show/NCT02118753?term=ischemia-reperfusion+injury>.

(56) References Cited

OTHER PUBLICATIONS

Steib, A., "Ischaemia-reperfusion During the Coronary Surgery With Beating Heart." ClinicalTrials.gov, Jan. 2013, University Hospital, Strasbourg, France, 67091, < https://clinicaltrials.gov/ct2/show/NCT01771978?term=ischemia-reperfusion+injury>.

Villar, J., et al., "Effects of induced hypothermia in patients with septic adult respiratory distress syndrome." Resuscitation, 1993, 26: 183-192.

Wang, W., et al., "Netrin-1 and kidney injury. I. Netrin-1 protects against ischemia-reperfusion injury of the kidney." Am J Physiol Renal Physiol, 2008, 294(4): F739-F747.

Wu, X., et al., "Systemic Hypothermia, but Not Regional Gut Hypothermia, Improves Survival from Prolonged Hemorrhagic Shock in Rats." J Trauma, 2002, 53: 654-662.

Wu, X., et al., "Mild hypothermia during hemorrhagic shock in rats improves survival without significant effects on inflammatory responses." Crit Care Med, 2003, 31(1): 195-202.

\* cited by examiner

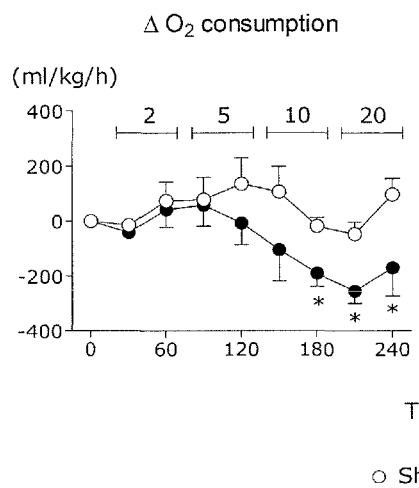
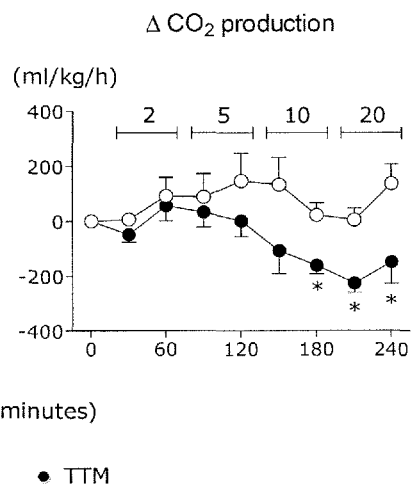
Fig. 1A         Fig. 1B
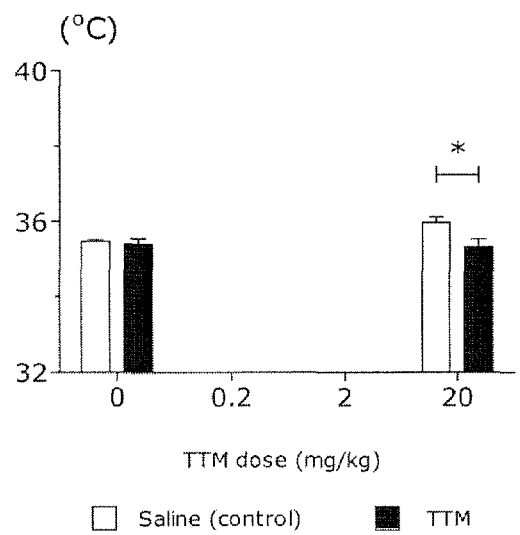
Fig. 2

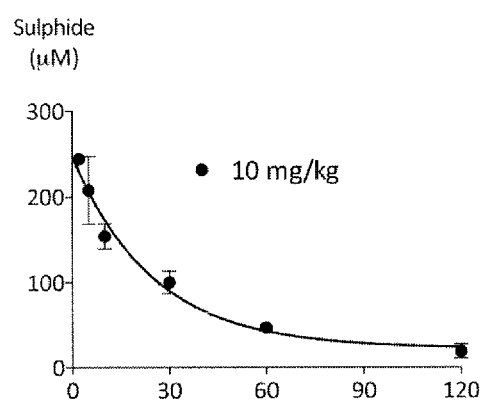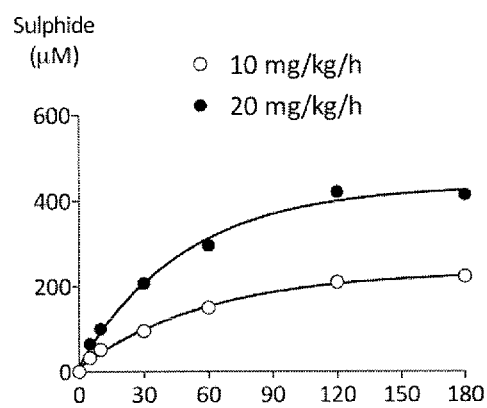
Fig. 5A                    Fig. 5B

THERAPEUTIC USE OF TETRATHIOMOLYBDATE

CROSS-REFERENCE TO A RELATED APPLICATION

This application is a continuation-in-part of International Application PCT/GB2011/050653, filed Mar. 30, 2011; which claims priority to European Patent Application 1005394.0, filed Mar. 30, 2010; this application also claims priority to European Patent Application No. 11183830.6, filed Oct. 4, 2011; all of which are incorporated by reference herein in their entirety.

FIELD OF THE INVENTION

This invention relates to therapy and, in particular, to the use of a known compound in the treatment of patients that have undergone an event such as myocardial infarction, stroke, cardiac arrest, severe haemorrhage or trauma. It may be especially useful to ameliorate the adverse effects of routinely used reperfusion/resuscitation strategies, for example angioplasty, thrombolysis, or bypass grafting following acute myocardial infarction.

BACKGROUND OF THE INVENTION

Experimental evidence suggests that hypothermia may be beneficial in shock by reducing organ metabolism and increasing the tolerance to ischaemia. Wu et al., J Trauma 2002; 53:654-62, compared regional (gut) and systemic hypothermia on survival in a rat haemorrhage model. They found that inducing systemic hypothermia increased 72 h survival time (100%) compared with regional hypothermia (25%) and normothermia (0%). In a follow-up study, the same group, in Wu et al., Crit Care Med 2003; 31:195-202, showed that hepatic injury was reduced.

Childs et al., J Trauma 2005; 58:271-7, show that hypothermia protects against microvascular barrier dysfunction and reactive oxygen species production. Ning et al., Am J Physiol Heart Circ Physiol 2003; 285:H212-H219, showed improved myocardial performance in isolated rabbit hearts subjected to hypoxia and reoxygenation during hypothermia compared with normothermic controls. Those under hypothermic conditions recovered better in terms of decreased coronary flow, oxygen consumption and developed pressure.

In a rodent model of experimental sepsis induced by caecal ligation and puncture, survival time was inversely proportional to body temperature from 32-42° C.; see L'Her et al., Crit Care Med 2006; 34:2621-3. The utility of hypothermia has also been demonstrated clinically. Hypothermic circulatory arrest is used in some forms of vascular surgery such as aortic arch repair to decrease metabolism and protect against cerebral ischaemia; see Haverich and Hagl., J Thorac Cardiovasc Surg 2003; 125:460-2.

In human sepsis associated with the acute respiratory distress syndrome, a subset of moribund patients was subjected to hypothermia as a 'last resort'; hypothermia (32-35° C.) improved survival compared with normothermic septic patients (67% vs 100%); see Villar and Slutsky, Resuscitation 1993; 26:183-92.

Tetrathiomolybdate (TTM) is known as a therapeutic agent. Brewer et al, Arch Neurol 2006; 63:521-7, discloses that ammonium TTM can be used to treat Wilson's disease, and that it preserves neurological function in patients who present with neurologic disease.

Brewer et al, Clin. Cancer Res 2000; 6:1-10, reports that TTM may be suitable in therapy of metastatic disease. Its utility apparently derives from its anti-copper activity.

SUMMARY OF THE INVENTION

According to the present invention, TTM is for use in therapy where reduced body metabolism, as achieved through reducing core temperature, is desirable. The therapy is thus, for example, potentially beneficial in cases of shock such as severe hypoxaemia and haemorrhage, trauma (e.g. head injury), and in reperfusion injury conditions (such as resuscitation after cardiac arrest, haemorrhage-reperfusion injury, and in elective vascular and cardiac surgery surgery involving interruption and re-institution of blood flow). This treatment may be applicable both in hospital or en route, e.g. in an ambulance. Clinical applications of particular interest are those surrounding ischaemia-reperfusion injury conditions such as those involving the brain (e.g. stroke, cardiac arrest, head injury), heart (e.g. during coronary artery bypass surgery and other types of open heart surgery, revascularisation after coronary artery thrombosis), and leg and kidney (e.g. following aortic cross-clamping for peripheral vascular surgery, or transplantation). The subject invention may be especially useful to ameliorate the adverse effects of routinely used reperfusion/resuscitation strategies, for example angioplasty, thrombolysis, or bypass grafting following acute myocardial infarction.

Without prejudice to the more general principle, that TTM would be therapeutically useful whenever blood flow is restored to an organ, an embodiment of the present invention of particular interest lies in the use of TTM as an adjunct to the therapy of myocardial infarction, with a view to mitigating the effects of reperfusion or revascularisation. For the purposes of this specification the term "revascularisation" means restoration of blood supply to an organ; examples are to the myocardium by angioplasty, coronary artery bypass grafting, retrograde coronary sinus perfusion, lasering of the myocardium or coronary artery thrombectomy; to the peripheral circulation by angioplasty or bypass grafting; and to the brain or kidney or liver by angioplasty.

This discovery is based on a showing that, during intravenous infusion of TTM into awake rats, there was a reduction in metabolism reflected by a decrease in oxygen consumption and carbon dioxide production. Notably, conscious level was maintained in the awake animals so this effect was not due to sedation. In anaesthetised rats, administration of TTM induced a fall in core temperature. Importantly, it was also observed that TTM ablates the hyperthermic response to endotoxin and even causes hypothermia when administered at 20 mg/kg in endotoxaemic animals.

BRIEF DESCRIPTION OF THE DRAWINGS

FIGS. 1A and 1B: Metabolic effects of TTM. Data show change in oxygen consumption (FIG. 1A) and carbon dioxide production (FIG. 1B) from baseline values.

FIG. 2: Core temperature at the beginning and end of an experiment where TTM was administered at increasing doses every 20 minutes.

FIGS. 5A and 5B. Plasma sulphide in rats following i.v. administration of TTM. FIG. 5A. Bolus dose (10 mg/kg). FIG. 5B. Continuous infusion (10 or 20 mg/kg/h).

FIG. 7A, survival time post-resuscitation; FIG. 7B, core temperature. BL; baseline, SH; end of the shock period, CTR; control (placebo-treated).

DESCRIPTION OF PREFERRED EMBODIMENTS

Figure 3:
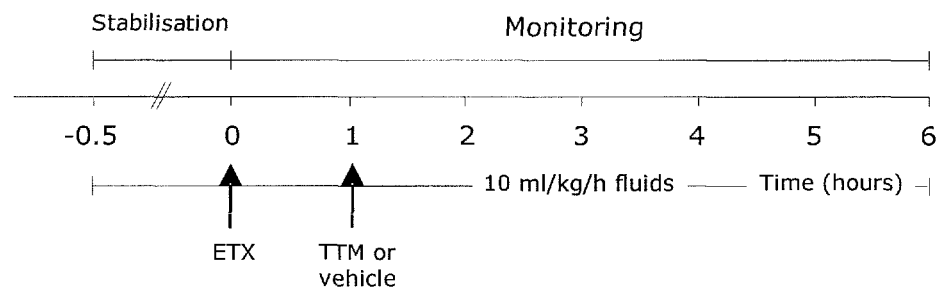
FIG. 3: Protocol for endotoxaemia experiments. ETX is endotoxin, TTM is tetrathiomolybdate. Fluids: a 50:50 mix of colloid and crystalloid plus glucose. TTM was diluted in normal saline and administered as a 4 ml/kg bolus.

As indicated above, a preferred embodiment is the use of TTM as an adjunct to the therapy of MI. For this purpose, MI can be treated in known manner, e.g. by percutaneous coronary intervention (angioplasty). This therapy is complemented by the simultaneous or separate administration of TTM.

TTM may be used as such or in the form of a pharmaceutically acceptable salt. Salts include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts. A particular salt is ammonium TTM.

A typical dosage is 2 to 20 mg/kg, administered one or more times per day or by continuous infusion. The drug is preferably administered via the intravenous route. It will be understood, however, that the specific dose level for any particular patient will depend upon a variety of factors including the age, body weight, general health, sex, diet, time of administration, drug combination and the severity of the particular condition undergoing therapy.

A pharmaceutical composition containing the active ingredient may be in any suitable form, for example aqueous or non-aqueous solutions or suspensions, dispersible powders or granules, transdermal or transmucosal patches, creams, ointments or emulsions.

The pharmaceutical composition may be in the form of a sterile injectable aqueous or non-aqueous (e.g. oleaginous) solution or suspension. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, phosphate buffer solution, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables. Suspensions may be formulated according to the known art using those suitable dispersing or wetting agents and suspending agents that have been mentioned elsewhere.

Aqueous suspensions contain the active ingredient in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Non-aqueous (i.e. oily) suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are known.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

The active agent may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials are cocoa butter and polyethylene glycols.

For topical delivery, transdermal and transmucosal patches, creams, ointments, jellies, solutions or suspensions may be employed. For sub-lingual delivery, fast dissolving tablet formulations may be used, as well as a number of the presentations described above. For oral administration, the drug may be administered as tablets, capsules or liquids.

The following Studies provides evidence on which the present invention is based.

Study 1

Male Wistar rats (300 g) were anaesthetised and instrumented with a venous line for drug administration. The animals were placed into a metabolic cart and allowed to recover from anaesthesia. After 2 h, TTM was administered i.v. hourly at increasing doses (2, 5, 10 and 20 mg/kg). Oxygen consumption and carbon dioxide production were continually monitored for the duration of the experiment. TTM induced a clear drop in oxygen consumption and carbon dioxide production at 10 and 20 mg/kg (FIG. 1), compared to time-matched control animals (sham) receiving only vehicle (saline).

Study 2

Animals were anaesthetised and instrumented as above. Under continuous anaesthesia, TTM was administered every 20 minutes at increasing doses (0.2, 2 and 20 mg/kg). Core temperature was measured at the beginning of the experiment (i.e. before TTM administration) and 20 minutes after the last dose of the drug (20 mg/kg). A decrease in core temperature was introduced by TTM (FIG. 2), compared to animals receiving vehicle (saline).

Study 3

Figure 4:
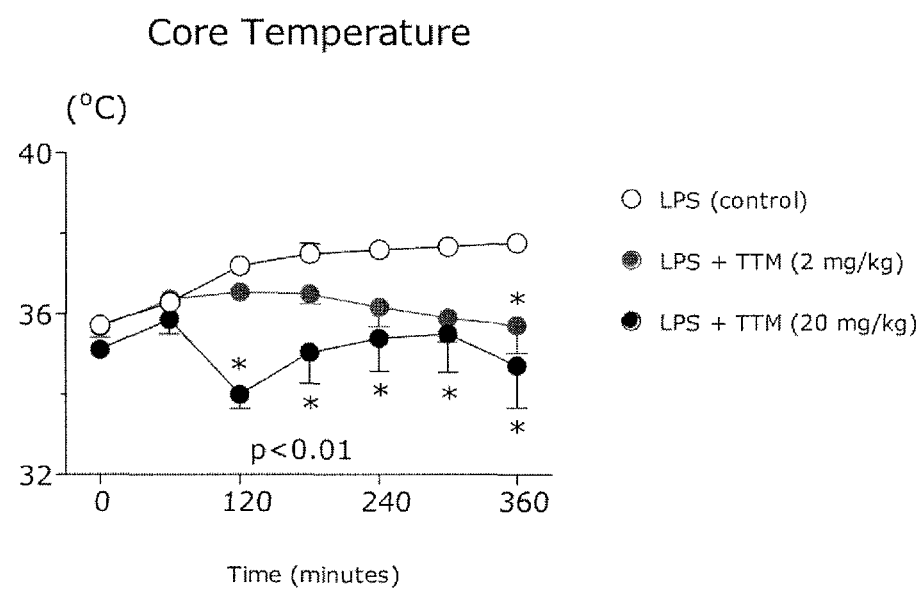
FIG. 4: Core temperature during endotoxaemia. TTM or vehicle was administered 60 minutes following the onset of endotoxaemia.

Animals received a venous line for drug administration under anaesthesia. Endotoxaemia (which typically causes an increase in core temperature) was induced by intravenous administration of lipopolysaccharide (20 mg/kg, *Klebsiella pneumoniae*). TTM or vehicle was administered 1 h following the onset of endotoxaemia (FIG. 3; protocol). Administration of TTM ablated the hyperthermic response to endotoxin observed in control animals and induced significant hypothermia at the highest dose (20 mg/kg) (FIG. 4).

Study 4

This study investigated sulphide release from tetrathiomolybdate (TTM). Male Wistar rats were anaesthetized allowing insertion of carotid arterial and jugular venous lines for blood sampling and drug administration, respectively. Plasma sulphide levels (measured using a monobromobimane-based HPLC assay) were determined up to 2 h following bolus i.v. administration of TTM (10 mg/kg) or for 3 h after the onset of two continuous i.v. infusions (10 and 20 mg/kg/h). TTM administration as a bolus (10 mg/kg) gave high levels of sulphide in plasma with a half-life of 17 minutes (FIG. 5A). Continuous infusion of TTM gave a dose-dependent increase in plasma sulphide levels that reached steady state after 2 h (FIG. 5B). These data confirm that TTM, when administered i.v., releases sulphide into the circulation.

Study 5

Figure 6:
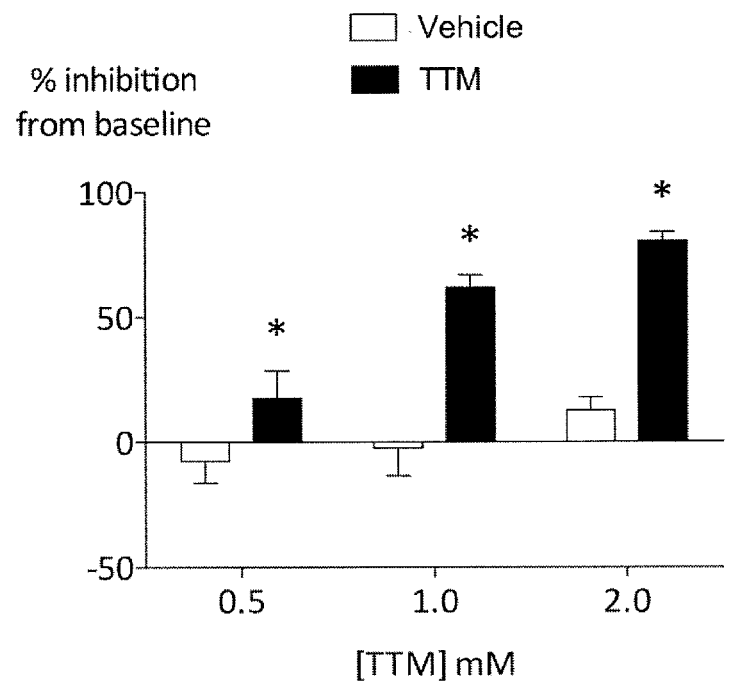
FIG. 6: TTM effect on oxygen consumption ex vivo.

This study investivated ex-vivo Inhibition of oxygen consumption by TTM. Soleus muscle was removed from the hind limbs of male Wistar rats and preserved on ice in a physiological buffer solution. Muscle fibres were isolated with forceps and permeabilized with saponin. Muscle fibres were placed in a closed chamber containing a physiological solution and substrates for oxidative metabolism. Oxygen concentrations within the chamber were measured using a Clark electrode. The fall in oxygen concentration over time (gradient) reflects oxygen consumption by the tissue. Either vehicle or TTM (0.5-2 mM) was added to the chamber and oxygen consumption assessed. TTM caused a dose-dependent inhibition of oxygen consumption ex vivo (FIG. 6). This further highlights the ability of TTM to decrease metabolism.

Study 6

Figures 7A, 7B:
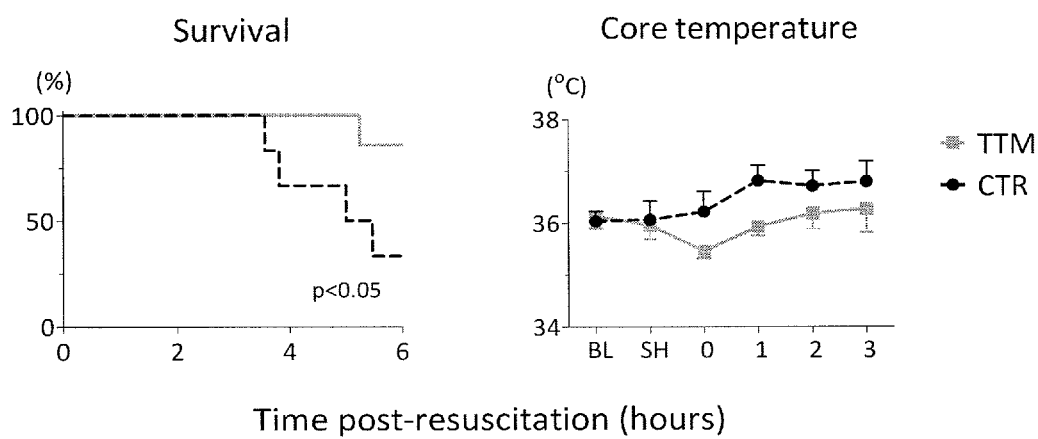
FIGS. 7A and 7B: Effects of TTM in a rat model of haemorrhage/reperfusion injury.

This study investigated effects of TTM in a rat model of haemorrhage/reperfusion injury. Male Wistar rats were anaesthetized for insertion of carotid arterial and jugular venous lines for blood removal and fluid/drug administration, respectively. After 30 min stabilization, 50% estimated circulating blood volume was removed from the arterial line over 15 min. Animals were monitored for a further 90 min prior to resuscitation, then randomized to receive either TTM or placebo (normal saline). TTM (10 mg/kg) was administered as an i.v. bolus (2 ml/kg). This was immediately followed by administration of shed blood over 15 min. In TTM-treated animals, the shed blood was supplemented with a further 2.5 mg/kg TTM; total dose 12.5 mg/kg. Placebo treated animals received equivalent volumes of fluid and administration of shed blood. Following resuscitation, both groups of animals received 10 ml/kg/h n-saline and were monitored up to 6 h post-resuscitation. Animals receiving TTM showed a significant improvement in 6 h survival (FIG. 7, left panel). Core temperature fell in TTM-treated animals (FIG. 7, right panel). Thus, TTM administration improves outcome following severe haemorrhage/reperfusion injury. This beneficial effect is potentially mediated by modulation of metabolism.

We claim:

1. A method for acute treatment of ischemia-reperfusion injury (IRI) in a subject that has undergone ischemic injury and is now at risk for acute injury caused by reperfusion following said ischemic injury, wherein said method comprises administering, to said subject, tetrathiomolybdate (TTM), via continuous infusion, wherein a total dose of up to 20 mg/kg TTM is administered to the subject over a period of one hour or less, such that within two hours of initiating treatment with TTM, there occurs in the subject a decrease in at least one of oxygen consumption and carbon dioxide production, thereby providing acute treatment of said IRI.

2. The method, according to claim 1, wherein the injury is of a head.

3. The method, according to claim 1, wherein the injury is of a brain.

4. The method, according to claim 1, wherein the treatment is for stroke.

5. The method, according to claim 1, wherein the injury is of a heart.

6. The method, according to claim 5, wherein the subject is undergoing a procedure selected from coronary artery bypass surgery, open heart surgery and treatment for coronary artery thrombosis.

7. The method, according to claim 1, wherein the injury is of a leg or kidney.

8. The method, according to claim 7, wherein the subject is undergoing aortic cross-clamping for peripheral vascular surgery.

9. The method, according to claim 1, wherein the treatment is for shock.

10. The method, according to claim 1, wherein the treatment is for hypoxemia.

11. The method, according to claim 1, wherein the treatment is for hemorrhage.

12. The method, according to claim 1, wherein the treatment is for cardiac arrest.

13. The method, according to claim 1, wherein the TTM is administered via intravenous administration.

* * * * *